US009134300B2

(12) United States Patent
Danias et al.

(10) Patent No.: US 9,134,300 B2
(45) Date of Patent: Sep. 15, 2015

(54) METHOD FOR SCREENING A DRUG IN RETINAL TISSUE (71) Applicant: Research Foundation of the City University of New York, New York, NY (US)

(72) Inventors: Ioannis Danias, Staten Island, NY (US); Hyungsik Lim, New York, NY (US)

(73) Assignees: Research Foundation of the City University of New York, New York, NY (US); Research Foundation of the State University of New York, Albany, NY (US)

( * ) Notice: Subject to any disclaimer, the term of this patent is extended or adjusted under 35 U.S.C. 154(b) by 0 days.

(21) Appl. No.: 14/306,898

(22) Filed: Jun. 17, 2014

(65) Prior Publication Data

US 2014/0295481 A1    Oct. 2, 2014

Related U.S. Application Data (63) Continuation of application No. PCT/US2012/070884, filed on Dec. 20, 2012.

(60) Provisional application No. 61/577,862, filed on Dec. 20, 2011.

(51) Int. Cl.
*G01N 33/50* (2006.01)
*G01J 9/00* (2006.01)
*G01J 4/00* (2006.01)
(Continued)

(52) U.S. Cl.
CPC .............. *G01N 33/5044* (2013.01); *A61B 3/10* (2013.01); *A61B 5/4848* (2013.01); *G01J 4/00* (2013.01); *G01J 9/00* (2013.01); *G01N 21/1717* (2013.01); *G01N 21/21* (2013.01); *G01N 21/63* (2013.01); *G01N 21/636* (2013.01); *G01N 33/4833* (2013.01); *G01N 33/5008* (2013.01); *G01J 2009/002* (2013.01); *G01J 2009/004* (2013.01); *G01N 2021/1734* (2013.01); *G02B 21/002* (2013.01)

(58) Field of Classification Search
CPC ..................... G01J 2004/001; G01J 2004/008; G02B 2207/114
See application file for complete search history.

(56) References Cited

U.S. PATENT DOCUMENTS 6,810,140 B2    10/2004  Yang et al.
7,109,208 B2 *   9/2006  Takayama et al. ............ 514/300
(Continued)

OTHER PUBLICATIONS

Aït-Belkacem et al., "Influence of birefringenece on polarization resolved nonlinear microscopy and collagen SHG structural imaging," Jun. 28, 2010, Optics Express, vol. 18, No. 14, pp. 14859-14870.*

(Continued)

*Primary Examiner* — Gordon J Stock, Jr.
(74) *Attorney, Agent, or Firm* — Peter J. Mikesell; Schmeiser, Olsen & Watts, LLP (57) ABSTRACT

The subject matter disclosed herein pertains to a method for screening drugs using second-harmonic generation microscopy. The tissue is scanned with a pulsed laser light which has an excitation wavelength. At least some of microtubules within the tissue produce generated light with a second-harmonic wavelength that is half the excitation wavelength. A microtubule pattern within the tissue is determined based on an analysis of the generated second-harmonic wavelength.

18 Claims, 8 Drawing Sheets

(51) Int. Cl.
- *G01N 33/483* (2006.01)
- *G01N 21/63* (2006.01)
- *G01N 21/17* (2006.01)
- *G01N 21/21* (2006.01)
- *A61B 5/00* (2006.01)
- *A61B 3/10* (2006.01)
- *G02B 21/00* (2006.01)

(56) References Cited

U.S. PATENT DOCUMENTS

| | | | |
|---|---|---|---|
| 7,510,283 B2 | 3/2009 | Bille | |
| 7,703,923 B2 | 4/2010 | Bille | |
| 8,137,271 B2 | 3/2012 | Bille | |
| 8,194,247 B2 * | 6/2012 | Sun et al. | 356/317 |
| 2002/0098518 A1 * | 7/2002 | Levinson | 435/7.1 |
| 2003/0148391 A1 * | 8/2003 | Salafsky | 435/7.2 |
| 2005/0063041 A1 * | 3/2005 | Sun et al. | 359/328 |
| 2005/0259249 A1 * | 11/2005 | Dombeck et al. | 356/300 |
| 2010/0031748 A1 | 2/2010 | Simpson et al. | |
| 2010/0204311 A1 | 8/2010 | Hayashi et al. | |

OTHER PUBLICATIONS

Sasaki et al., "Tomographic imaging of collagen fiber orientation in human tissue using depth-resolved polarimetry of second-harmonic-generation light," 2004, IEEE, THP-39(T8), pp. 205-206.*

Yew et al., "Second harmonic generation polarization microscopy with tightly focused linearly and radially polarized beams," 2007, Optics Communications 275, pp. 453-457.*

Lim, Hyungsik et al., "Effect of axonal micro-tubules on the morphology of retinal nerve fibers studied by second-harmonic generation," Nov. 2012, Journal of Biomedical Optics, vol. 17(11), pp. 110502-1-110502-3.*

Wang et al., Two-photon microscopy of deep intravital tissues and its merits in clinical research, Journal of Microscopy, 2010, vol. 238, pp. 1-20.

Baas et al., Hooks and comets: the story of microtubule polarity orientation in the neuron, Developmental Neurobiology, Jun. 2011, vol. 71, pp. 403-418.

ISA/KR, International Search Report from PCT/US2012/070884 as completed on Apr. 5, 2013 (total 3 pgs).

Dombeck, Daniel A. et al., "Uniform polarity microtubule assemblies imaged in native brain tissue by second-harmonic generation microscopy", PNAS, Jun. 10, 2003, vol. 100, No. 12, pp. 7081-7086 (total 6 pgs).

Fortune, Brad et al., "Relative Course of Retinal Nerve Fiber Layer Birefringence an Thickness and Retinal Function Changes after Optic Nerve Transection", Investigative Ophthalmology & Visual Science, Oct. 2008, vol. 49, No. 10, Coyright Association for Research in Vision and Ophthalmology, 9 pgs.

Brown, Donald J. et al., "Application of second harmonic imaging microscopy to assess structural changes in optic nerve head structure ex vivo", Journal of Biomedical Optics Mar./Apr. 2007, vol. 12(2) DOI: 1083-3668/2007/12(2)/024029/5/$25.00, Copyright 2007 SPIE, 5 pgs.

Kwan, Alex C. et al., "Polarized microtubule arrays in apical dendrites and axons", PNAS, Aug. 12, 2008, vol. 105, No. 32, pp. 11370-11375, 6 pgs. Found also at www.pnas.org/cgi/doi/10.1073/pnas.0805199105.

Campagnola, Paul J. et al., "High Resolution Nonlinear Optical Imaging of Live Cells by Second harmonic Generation", Biophysical Journal, vol. 77, Dec. 1999, pp. 3341-3349, 9 pgs.

Lim, Hyungsik et al., "Label-free morphometry of retinal nerve fiber bundles by second-harmoni-generation microscopy", Copyright 2012 Optical Society of America, #0146-9592/12/122316-03$15.00/0, Posted Apr. 2, 2012 (Doc. ID: 165284); published Jun. 8, 2012, 3 pgs.

* cited by examiner

METHOD FOR SCREENING A DRUG IN RETINAL TISSUE

CROSS-REFERENCE TO RELATED APPLICATIONS

This application is a continuation of international patent application number PCT/US2012/070884 (filed Dec. 20, 2012) which claims priority to and the benefit of U.S. provisional patent application Ser. No. 61/577,862 (filed Dec. 20, 2011). These applications are hereby incorporated by reference in their entirety.

STATEMENT REGARDING FEDERALLY FUNDED RESEARCH OR DEVELOPMENT

This invention was made with government support under contract number NEI EY15224 awarded by the National Eye Institute of the National Institute of Health (NIH). The government has certain rights in the invention.

FIELD OF THE INVENTION

This invention relates, in one embodiment, to a method of determining a microtubule pattern using second-harmonic generation microscopy. In one embodiment, the method is utilized on retinal tissues to detect, diagnose, or rapidly screen drugs that alter the microtubule pattern within the retina.

BACKGROUND

Glaucoma is the leading cause of irreversible blindness worldwide. It is a retinal neurodegenerative disorder where retinal ganglion cells (RGC) and their axons (that form the optic nerve) are lost. Even though elevated intraocular pressure is a known risk factor and an observed symptom for the disease, such pressure measurements are not reliable for diagnosing glaucoma. Current psychophysical methods used in clinical practice for detecting glaucoma depend on the occurrence of significant progressive loss of axons with approximately 40% of optic nerve axons needing to be lost before a functional change in peripheral vision can be clinically detected. Clearly, these current methods cannot detect the early onset of the disease as they depend on the patient's ability and cooperation to identify the areas of functional defects in the field of vision. Additional methods to detect and diagnose glaucoma are desired. Several objective imaging techniques have been developed in an attempt to address this need.

Scanning laser polarimetry (SLP), confocal scanning laser ophthalmoscopy (CSLO) and optical coherence tomography (OCT) are used for this purpose. They either measure the charges that occur in the optic nerve head or the thickness of the retinal nerve fiber layer (RNFL). Methods that image/measure the retinal nerve fiber layer utilize birefringence/interferometric based methods and are hindered by the limitations of such methods including phrase wrapping artifacts and poor signal-to-noise ratio. Additionally, the disease must progress to the point where a morphological change in the retinal nerve fiber layer can be detected. An alternative technique for the early detection of glaucoma is therefore desired that addresses at least some of these shortcomings.

SUMMARY OF THE INVENTION

The subject matter disclosed herein pertains to a method for determining a microtubule pattern using second-harmonic generation (SHG) microscopy. The tissue is scanned with a pulsed laser light which has an excitation wavelength. At least some of microtubules within the tissue produce generated light with a second-harmonic wavelength that is half the excitation wavelength. A microtubule pattern within the tissue is determined based on an analysis of the generated second-harmonic wavelength.

An advantage that may be realized in the practice of some disclosed embodiments of the method is the ability to monitor microtubules at the molecular level and thereby detect and/or diagnose diseases or responses to drugs at a very early stage.

BRIEF DESCRIPTION OF THE DRAWINGS

The present invention is disclosed with reference to the accompanying drawings, wherein:

FIG. 8A is a graph showing the intensity of the second-harmonic generating signal from retinal ganglion cells signal depends on the polarization of excitation wavelength while

Corresponding reference characters indicate corresponding parts throughout the several views. The examples set out herein illustrate several embodiments of the invention but should not be construed as limiting the scope of the invention in any manner.

DETAILED DESCRIPTION

Figure 1:
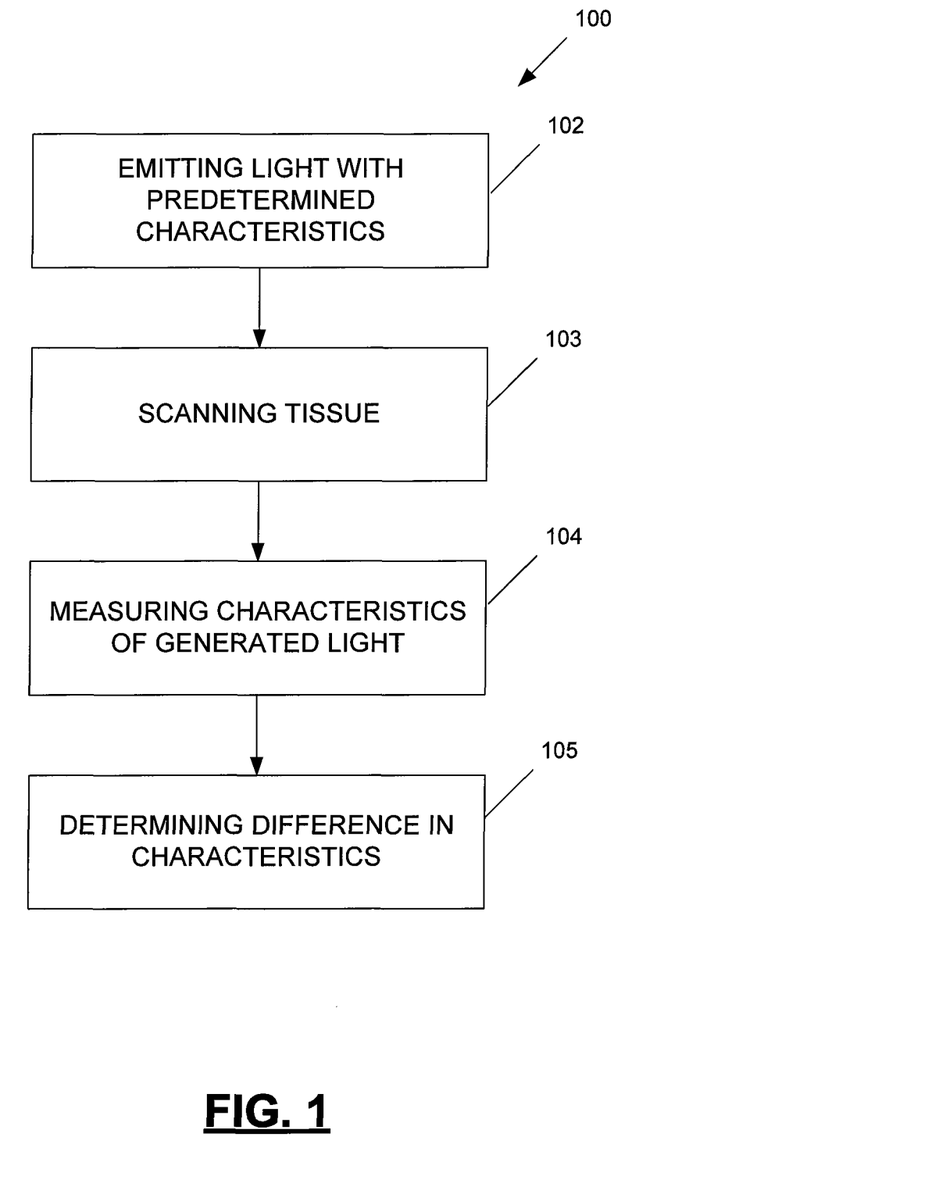
FIG. 1 is a flow diagram of an exemplary method for determining a microtubule pattern in a retinal tissue.

FIG. 1 is a flow diagram of an exemplary method 100 for scanning a retinal nerve fiber layer (RNFL) of a retinal tissue using label-free second-harmonic generation (SHG) microscopy. A SGH signal is sensitive to microtubule structure. Because the healthy retina exhibits a highly organized microtubule pattern while glaucomatous retina does not, the second-harmonic generation signal reports the condition of the retina nerve fiber layer.

Method 100 comprises step 102 wherein a pulsed laser light is emitted. The pulsed laser light has one or more predetermined characteristics including a predetermined excitation wavelength, a predetermined polarization and/or a predetermined spatial mode. When the excitation wavelength interacts with the microtubules in step 103, those microtubules that are uniformly oriented return light with a second-harmonic wavelength that is half the excitation wavelength. In addition to the wavelength, one or more of the other predetermined characteristics of the excitation wavelength may also be altered, depending on the structure of the microtubules. These altered characteristics are measured in step 104, when the generated light returned by the microtubules is analyzed. Since only uniformly oriented microtubules produce second harmonic generation signals, detection of the second-harmonic wavelength provides a mechanism to determine the uniformity of oriented microtubules as well as the structural integrity of the microtubules. In step 105 the difference between the characteristics of the excitation wave (e.g. its spatial mode or its polarization) and the corresponding characteristics of the generated light is determined. This difference provides additional structural information about the microtubules and provides an early detection mechanism for microtubule-related diseases.

Figure 2A:
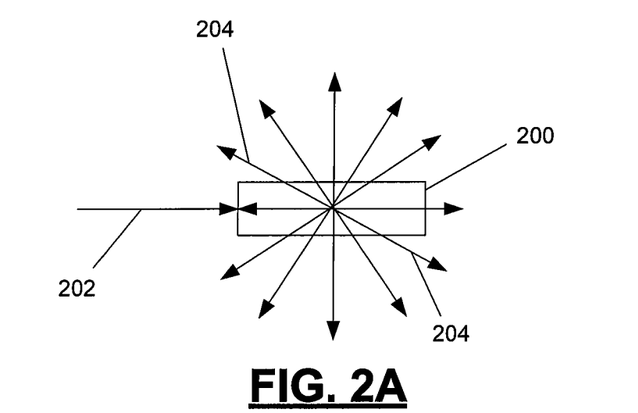
FIG. 2A and FIG. 2B are schematic illustrations of two optical mechanisms pertaining to the subject matter disclosed herein.
Figure 2B:
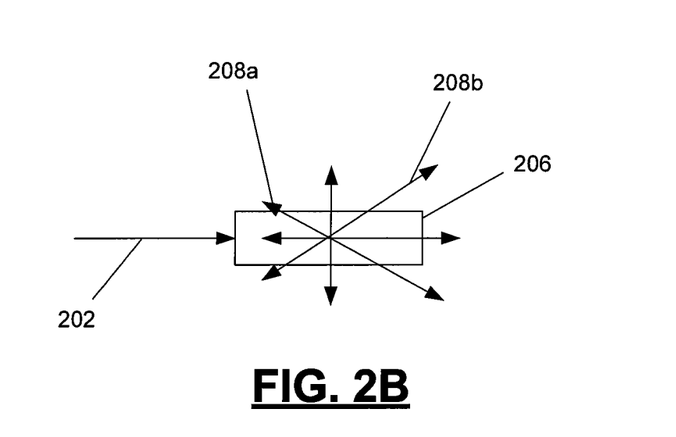

In one embodiment, the second-harmonic wavelength is analyzed to determine a microtubule pattern within the retinal tissue. The determination makes use of microscopy to determine the two-dimensional or three-dimensional location of microtubules. Additionally or alternatively, the determination may analyze the intensity of the generated light at the second-harmonic wavelength to provide a quantitative value that corresponds to an amount of uniformly orientated microtubules within a volume of tissue. The microtubule pattern provides useful information concerning the molecular state of the microtubules which, in turn, provides useful information concerning certain disease states, including glaucoma. By analyzing only the second-harmonic wavelength, extraneous wavelengths, including the excitation wavelength, are omitted. The resulting microtubule pattern is therefore highly specific to microtubules, and uniformly oriented microtubules in particular. FIG. 2A and FIG. 2B are schematic illustrations of the optical mechanisms that provides this specificity.

FIG. 2A is a schematic illustration of an object 200 that is exposed to excitation wavelength 202 and, in response, produces fluorescence wavelengths 204. Object 200 may be any object that undergoes fluorescence, including non-uniformly oriented microtubules, such as microtubules in glaucomatous tissues. As would be apparent to those skilled in the art, the distribution of fluorescence wavelengths 204 is symmetrical in all directions. Additionally, the wavelength (color) of the fluorescence wavelengths 204 is not the same as the excitation wavelength 202 but is a function of the electronic structure of the molecular orbitals of object 200 and has a longer wavelength than the excitation wavelength.

FIG. 2B is a schematic illustration of an object 206 that is exposed to the excitation wavelength 202 and, in response, produces a second-harmonic wavelength 208a and 208b. Object 206 may be any object that undergoes second-harmonic generation, including uniformly oriented microtubules.

Second-harmonic generation microscopy is based on the eponymous coherent process, where two photons are combined to produce one photon with twice the energy. Second-harmonic generation is a second-order, nonlinear optical process which uses high concentration of non-centrosymmetric molecules (e.g. uniformly orientated microtubules) that are uniformly oriented. Second-harmonic generation microscopy has a number of advantages in tissue imaging. Because of the nonlinear nature of the process, signal light is emitted only from a tight focal volume. The localized excitation not only allows construction of three-dimensional morphology with sub-pm resolutions, but also reduces out-of-focus photodamage. Moreover, the excitation wavelength may be in the near infrared (MIR) (within the so-called "biological window") where tissue exhibits significantly less scattering and absorption. Not only does near infrared excitation enable deeper penetration into the tissue, but also the safety of laser illumination is higher at longer near infrared wavelengths.

Second-harmonic generation signals exhibit characteristics that are distinct from birefringence signals including (1) being predominantly forward-propagating (e.g. wavelength 208b) including an angle from the optical axis due to Gouy's phase shift through the beam focus with a smaller portion of the generated light being backward-propagating (e.g. wavelength 208a), (2) a dependency on the polarization of the excitation wavelength due to the relative orientation between light polarization and the uniformly orientated microtubules (3) the return of a second-harmonic wavelength that is solely determined by the excitation wavelength such that it is half the excitation wavelength and (4) the intensity of the generated light has quadratic dependencies on the excitation wavelength.

Applications of the methods disclosed herein include the early detection of glaucoma, even before loss of axons. The technique described herein diagnoses glaucoma at the molecular level, and thus enables earlier detection of glaucoma than currently possible. A microtubule second-harmonic generation signal (MT-SHG), generated in the axonal microtubules, provides an endogenous imaging contrast by which the retinal nerve fibers can be seen without exogenous stains or genetic engineering. The technique may be performed in vivo on a tissue sample comprising a live retina or in vitro on a tissue sample. Axonal microtubule second-harmonic generation imaging of the retinal nerve fiber layer in vivo provides a means to quantitatively detect the physiological modifications in the microtubule assembly in the retinal ganglion cell. Because the process of microtubule second-harmonic generation imaging depends on the organization of axonal microtubules, the signal can measure the structural integrity of the axons, and therefore offers a unique capability in early-stage clinical detection, diagnosis, and research of retinal neurodegenerative diseases, such as early-stage glaucoma.

Other applications include screening of therapeutic drugs that alter microtubule patterns. The second-harmonic generation (SHG) signal from neurons can also be exploited to provide an intraoperative visual aid for thyroid cancer surgery, where identification of the nerve is compounded to result in inadvertent injury which leads to the loss of vocal innervations (i.e. inability to speak). A modified form of the disclosed second-harmonic generation instrument may be used to visualize the vocal nerves in the proximity of thyroid cancer. Still further applications include the diagnosis of diabetic retinopathy, central vein occlusion and other optic neuropathies (non glaucomatous), imaging of optic nerve fibers, detection of the ocular symptoms of Alzheimers' disease, multiple sclerosis, and the like. Additional applications would be apparent to those skilled in the art after benefitting from reading this specification.

Figure 3:
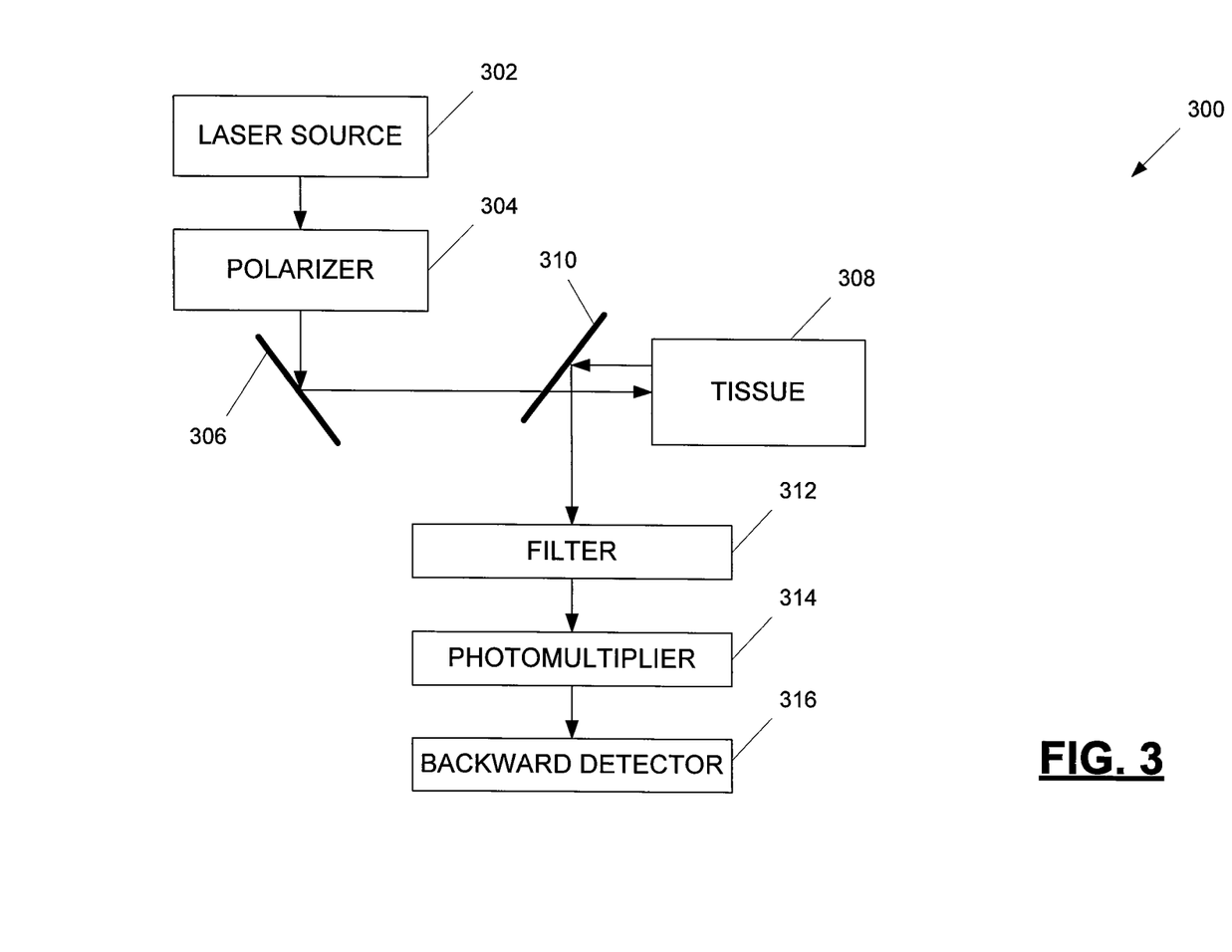
FIG. 3 is a flow diagram of an exemplary method for determining a microtubule pattern in a retinal tissue.

FIG. 3 is a schematic depiction of an exemplary system 300 for scanning a retinal tissue using label-free second-harmonic generation microscopy. An excitation wavelength exits laser source 302 (e.g. a Ti:Sapphire laser, a Ytterbium-doped fiber laser, and the like), is polarized by polarizer 304, and thereafter contacts beam scanner 306 which directs the resulting polarized, pulsed laser light through dichroic mirror 310. The pulsed laser light may have a pulse duration between 10 fs and 1 ns. In another embodiment, the pulsed laser light may have a pulse duration between 10 fs and 500 ps. In another embodiment the pulsed laser light may have a pulse duration between 10 fs and 10 ps. The pulsed laser light may have a repetition of between 1 KHz and 100 MHz. In another embodiment, the pulsed laser light may have a repetition of between 1 KHz and 80 MHz. In one embodiment, the pulsed laser light has a repetition of about 80 MHz. In one embodiment, the energy of the pulsed light is greater than zero but less than 1 nJ. In another embodiment the pulsed laser light has a repetition of between 1 KHz and 10 MHz. The excitation wavelength may be between 600 nm and 1500 nm. In another embodiment, the excitation wavelength is between 1300 nm and 1500 nm. The excitation wavelength has a relatively narrow bandwidth. In one embodiment, the bandwidth is about 10 nm or less. For example, the excitation wavelength may be 800 nm with a 20 nm bandwidth, resulting in a narrow range of frequencies between 790 nm and 810 nm. In another embodiment, the excitation wavelength may be 800 nm with a 10 nm bandwidth, resulting in a narrow range of frequencies between 795 nm and 805 nm. The resulting excitation wavelength interacts with tissue 308. These parameters permit scanning of microtubules while minimizing photodamage to the retinal tissue. This is particularly advantageously when the method is performed in vivo.

Using an excitation wavelength with a narrow bandwidth, a relatively broad range of wavelengths may be sequentially probed. For example, a portion of a retinal tissue may be scanned using an excitation wavelength of 800 nm with a bandwidth of 10 nm to determine the microtubule pattern of microtubules responsive to such an excitation wavelength. Thereafter, the excitation wavelength may be changed to, for example, 820 nm with a bandwidth of 10 nm and the process is repeated. In this fashion a broad range of wavelengths (e.g. 700 nm to 1100 nm) may be sequentially probed.

In an analogous fashion, one can sequentially probe over a range of polarization values to detect those microtubules that are responsive to a particular polarization. For example, retinal tissue may be scanned using a first excitation wavelength having a first polarity. Data for microtubules responsive to the first polarity is gathered. Thereafter, the retinal tissue may be scanned using the first excitation wavelength having a second polarity. Data for microtubules responsive to the second polarity is gathered.

The predetermined characteristics (e.g. polarization, spatial mode) of the excitation wavelength may be set anytime prior to the wavelength contacting the tissue 308. Tissue 308 may be a retinal tissue. In one embodiment, the retinal tissue is within the eye of a living human being. In another embodiment, the retinal tissue is within the eye of a living, non-human animal. In another embodiment, the retinal tissue is an extracted sample that may be from a human or an animal. In certain embodiments, second-harmonic generation from collagen in sclera may obscure the desired signal as collagen is another second-harmonic generation emitter. In one embodiment, the pulsed laser light is directed away from tissue with a high collagen concentration (e.g. the scelera) to minimize the interference. Such direction may be controlled by beam scanner 306.

In another embodiment, the excitation wavelength is directed through the sclera and the resulting second-harmonic generation signal is collected through the pupil. Advantageously, this takes advantage of the relatively strong forward-propagating signal of SHG. In an exemplary in vivo embodiment, the excitation wavelength is applied from the lateral aspect of the orbit (just anteriorly to the bony lateral rim of the orbit) while the patient looks toward his or her nose. In those embodiments where the wavelength is within the biological window, a degree of tissue penetration can be achieved. The resulting forward-propagating SHG light exits through the pupil of the eye. In another embodiment, the excitation wavelength comes from a fiberoptic probe that is illuminated on its side (e.g. ninety degrees to its longitudinal axis) that is inserted in the conjunctival cul de sac and is in touch with the sclera. The patient is asked to look ninety or more degrees away from the axis of the probe so that SHG signal can be collected through the pupil.

When the excitation wavelength interacts with tissue 308, the uniformly orientated microtubules within the tissue 308 produce generated light with a second-harmonic-wavelength, a portion of which is backward-propagating light. The second harmonic-wavelength is half the excitation wavelength. For example, when the excitation wavelength is 800 nm, the generated light has a second-harmonic wavelength of 400 nm. The second-harmonic generation signal may also have its characteristics (e.g. polarity, spatial mode) altered, relative to the corresponding characteristics of the excitation wavelength. The differences in these characteristics is a function of the microtubule structure.

The second harmonic-wavelength is directed along a different path than the excitation wavelength by the dichroic mirror 310 to a filter 312 which filters extraneous wavelengths, such as those from the environment. For example, when the excitation wavelength is 800 nm, it is known the second harmonic-wavelength will be 400 nm. Accordingly, the filter 312 is selected to filter out extraneous wavelengths other than 400 nm. Advantageously, this removes the excitation wavelength 800 that is produced by the laser source 302, backscattered light from the tissue 308 and well as other extraneous wavelengths. The filtered light is processed by a light processor 314 and thereafter provided to a photodetector, such as backward-propagating detector 316. The light processor 314 may include optical processing components such as photomultipliers, wave front modulators, polarizers, and the like. Light processor 314 is useful for detecting the characteristics of the second-harmonic generation signal, including the polarization and the spatial mode.

Other exemplary systems may comprise additional components including one or more of fiber optic devices, dispersion control elements to control the phase and duration of the excitation laser beam pulse, light modulator element switches to modulate the excitation laser beam, objective lenses to focus the pulsed laser light on a tissue, adaptive optics such as wavefront sensor (e.g. a Hartman-Shack sensor) and a wavefront modulator (e.g. deformable mirror), two-dimensional beam scanners for guiding the laser beam over the tissue surface; probes for insertion into an eye wherein the pulsed laser light is guided through the probe, optical compensators such as prisms, grating pair, photonic bandgap fibers to minimize the pulse distortion that arises from nonlinear effects.

Figure 4:
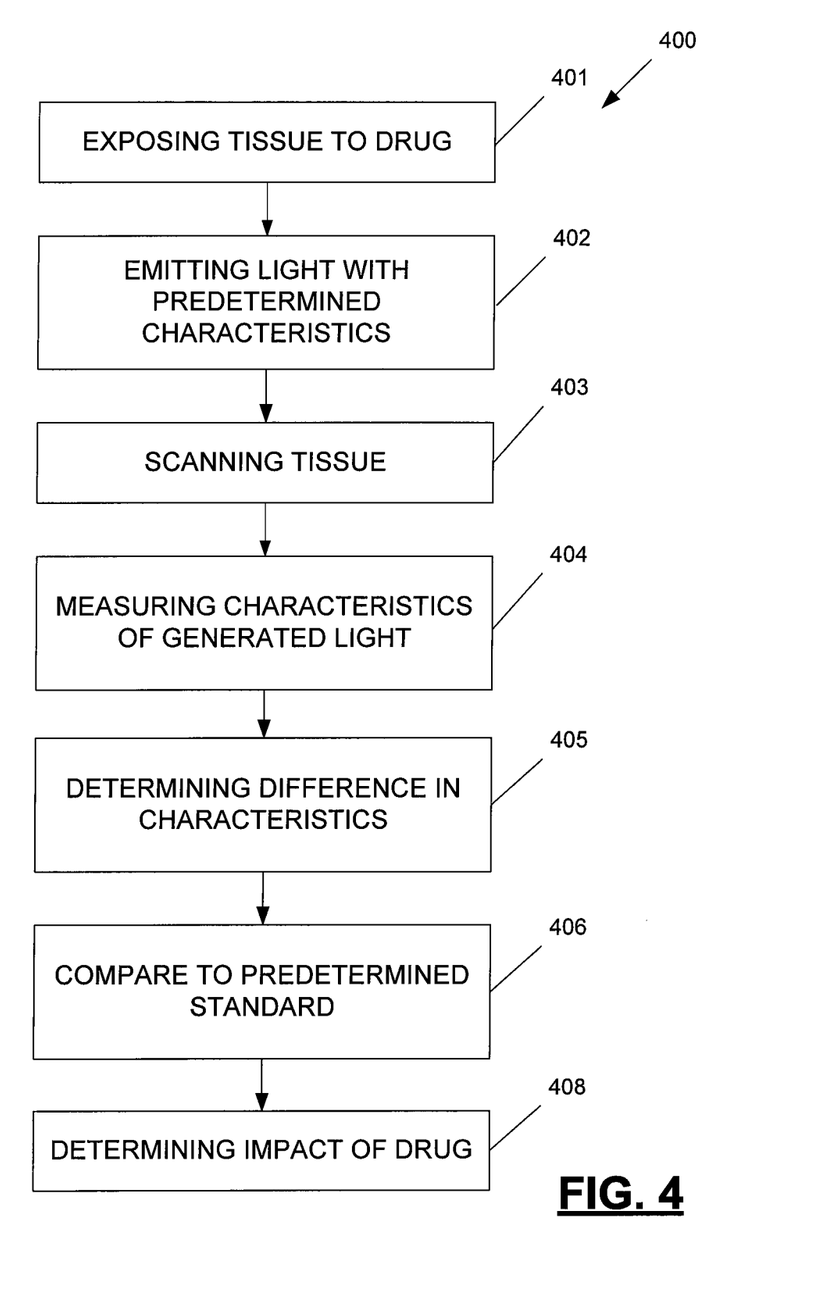
FIG. 4 is a flow diagram of an exemplary method for screening drugs by determining a microtubule pattern in a retinal tissue.

FIG. 4 is a flow diagram of an exemplary method 400 for screening drugs in a retinal tissue using label-free second-harmonic generation microscopy. The exemplary method 400 provides rapid data concerning the effectiveness of a drug on the microtubules of the tissue. This enables the effectiveness of drugs to be quickly screened using, for example, tissues from animal subjects (e.g. retinal tissues from rats). The method 400 begins with step 401 wherein a tissue, such as a retinal tissue, is exposed to a drug. In step 402, a pulsed laser light with predetermined characteristics (e.g. wavelength, polarization and/or spatial mode) is emitted. In step 403 the tissue is scanned with the pulsed laser light. In step 404, the characteristics of the generated light from the microtubules is measured. In step 405, the difference in the characteristics of the excitation wavelength and the generated light is determined.

In one embodiment, a first microtubule pattern is determined based on the generated light. In step 406 the first microtubule pattern is compared to a predetermined standard. In one embodiment, the predetermined standard is a placebo that functions as a control. In another embodiment, the predetermined standard is a previously recorded microtubule pattern from the same tissue (i.e. the microtubule patterns is monitored over time). In another embodiment, the predetermined standard is a second microtubule pattern from an analogous tissue (e.g. the tissue that is exposed to the drug is compared to a typical microtubule pattern from a tissue that is not exposed to the drug). For example, a diseased tissue that has been exposed to the drug may be compared to the typical microtubule pattern from a similarly diseased tissue that has not been exposed to the drug.

In step 408, the impact of the drug is determined based on the differences determined in step 405. For example, in step 408 it may be determined that the drug alters the characteristics of the generated light to more closely approximately the characteristics of generated light from a non-diseased tissue. Alternatively, it may be determined that the drug fails to alter the characteristics of the generated light relative to the predetermined standard. It may also be determined that the drug accelerates the progress of the disease.

Figure 5:
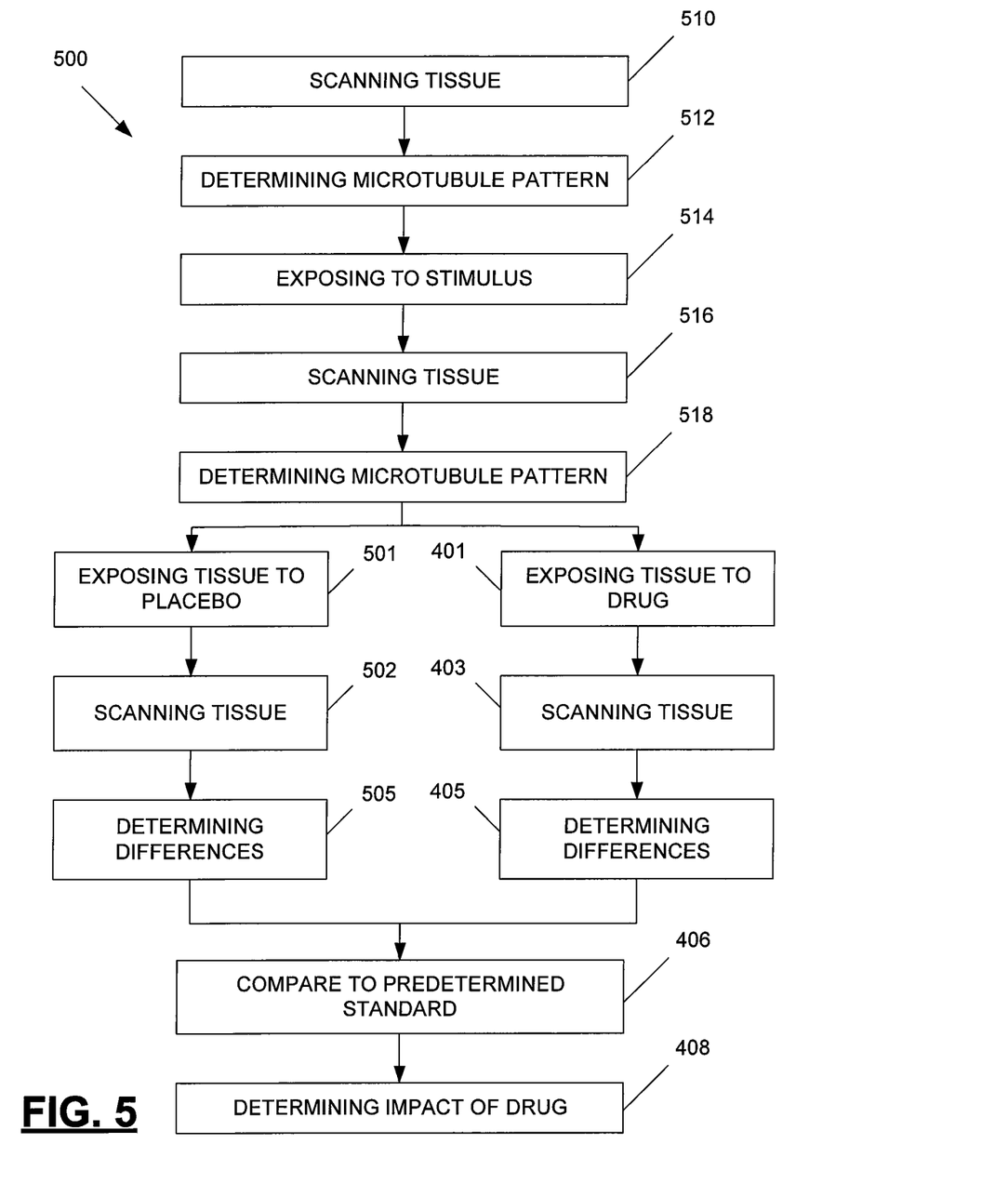
FIG. 5 is a flow diagram of another exemplary method for screening drugs by determining a microtubule pattern in a retinal tissue.

FIG. 5 is a flow diagram of an exemplary method 500 for screening drugs by determining a microtubule pattern in a retinal tissue using label-free second-harmonic generation microscopy. In method 500 a sample is prepared by scanning a retinal tissue (step 510) and determining its microtubule pattern (step 512). This step may be utilized to verify the integrity of the sample. In step 514, the retinal tissue is exposed to a stimulus that alters the microtubule pattern. Examples of suitable stimuli includes physical stimuli (e.g. altered pressure, changes in light exposure, etc) or chemical stimuli (e.g. a drug). The stimuli may be chosen to intentionally damage the microtubule pattern in preparation for subsequent testing. The alteration may be verified by rescanning (step 516) and re-determining (step 518) the microtubule pattern. In this fashion, a prepared retinal tissue sample is provided.

The prepared retinal tissue sample is divided into a first sample and a second sample. The first sample is subjected to method 400, including steps 401, 403 and 405. In a similar fashion, the second sample is exposed to placebo conditions (step 501), scanned (step 502) and its differences in characteristics are determined (step 505). This differences in the characteristics of the generated light from the second sample serves as a predetermined standard for comparison with the differences from step 405. In step 406, the differences in characteristics from step 405 is compared to the placebo-derived predetermined standard from step 505. In step 408, the impact of the drug (see step 401) on the microtubules is determined.

Figure 6:
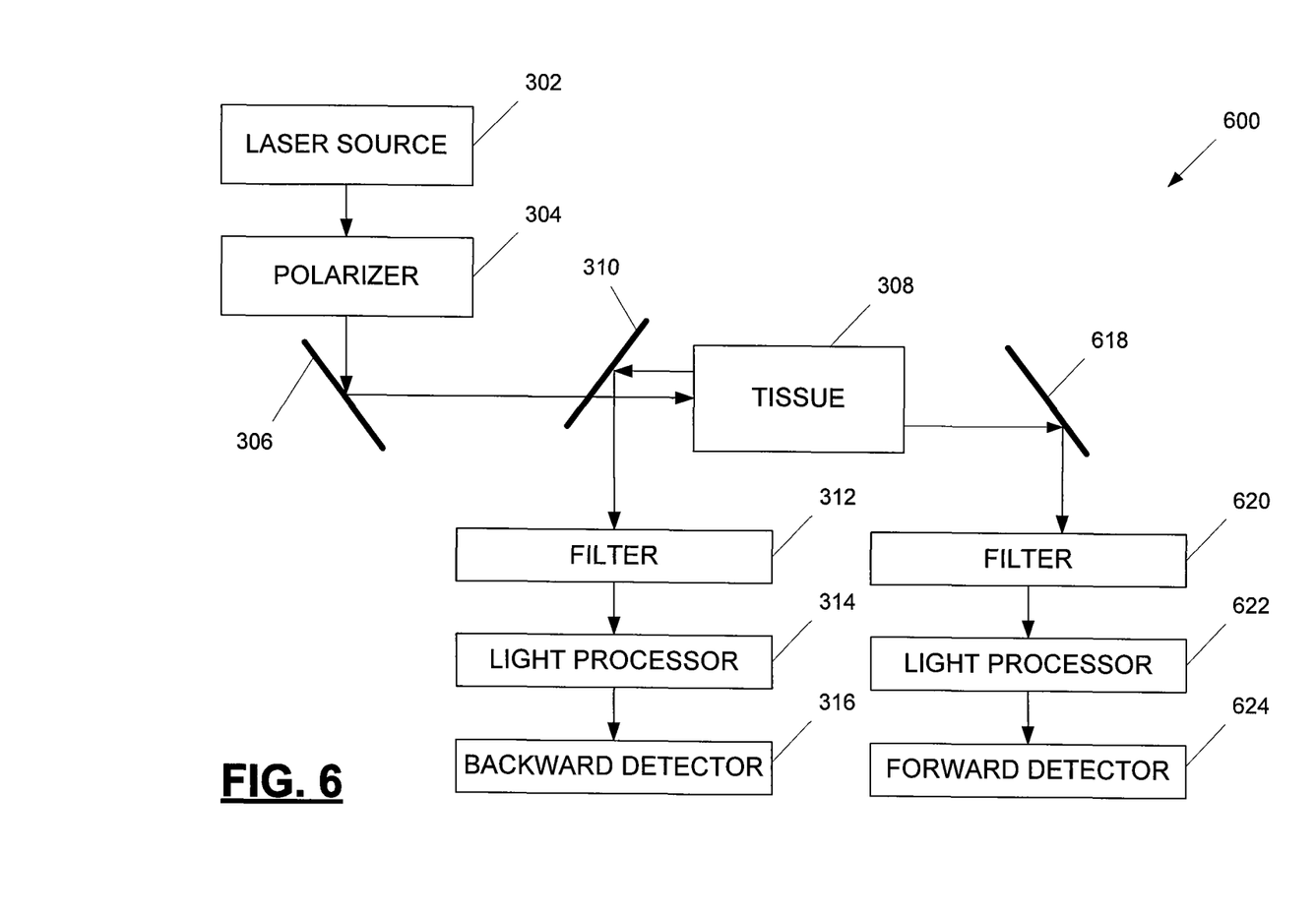
FIG. 6 is a schematic depiction of an exemplary system for determining a microtubule pattern in a retinal tissue.

FIG. 6 is a schematic depiction of an exemplary system 600 for determining a microtubule pattern in a retinal tissue using label-free second-harmonic generation microscopy. System 600 is analogous to system 300 of FIG. 3 but further includes components to permit analysis of forward-propagating wavelengths. In the exemplary embodiment of FIG. 6, forward-propagating wavelengths are directed using a beam scanner 618 to pass through a filter 620. In one embodiment, the filter 620 is analogous to filter 312. The filter 620 filters extraneous wavelengths, such as those from the environment. For example, when the excitation wavelength is 800 nm, it is known the second harmonic-wavelength will be 400 nm. Accordingly, the filter 620 is selected to filter out extraneous wavelengths other than 400 nm. In the exemplary embodiment of FIG. 6, the forward-propagating wavelengths are processed by light processor 622 which is analogous to light processor 314. The forward-propagating wavelengths contact forward detector 624 which detects the wavelength and permits determining of a microtubule pattern. The forward detector 624 is analogous to backward detector 316. In one embodiment, a photomultiplier is in-line with the forward detector 624. Additional components may be in the path of the forward-propagating wavelengths prior to the forward detector 624 including polarization optics.

In one embodiment, one or both of the detectors 316, 624, are configured to detect differential light properties, such as the polarization, spatial mode, and wavelength of either the excitation or returned second-harmonic generation light for the determination of a microtubule pattern in a retinal tissue. Interaction between light and molecules provides a means to determine the structure of molecule. The structural information can be encoded in the light (i.e. in the intensity, wavelength, and polarization) via any matter-light interaction that causes changes in energy, momentum, and angular momentum of light. Similarly, the way which microtubules respond to light can be utilized to learn about the microtubule pattern. A particular molecular and supramolecular pattern of microtubules leaves a distinctive imprint on the energy, momentum, and angular momentum of light.

Characteristics of Second-Harmonic Generated Light

In the case of second-harmonic generation (SHG), it is necessary that the molecular structure of the microtubule satisfies a certain condition, namely the lack of inversion symmetry. In general the nonlinear susceptibility coefficient underlying the second-harmonic generation is represented by second-order susceptibility $\chi^{(2)}$.

$$P_{SHG} = \chi^{(2)} : EE$$

$P_{SHG}$ is the (vector) amplitude of SHG light, E is the (vector) amplitude of excitation light. The second-order susceptibility $\chi^{(2)}$ is a property of the microtubule that is related to its molecular structure. It is a 3×3×3 tensor quantity with a total of 27 independent components. Each component depends on the specific aspects of the structure of SHG-emitting molecules. As a result, determination of individual tensor elements of $\chi^{(2)}$, for instance by polarization-sensitive SHG measurements, affords the characterization of molecular structure on the nanometer scales beyond the optical resolution limit set by diffraction. For example, the orientation axis and chiral angle of microtubules are among the structural parameters that can be determined by $\chi^{(2)}$ measurements. It is emphasized that some of these parameters cannot be obtained by any other methods. Furthermore, the molecular-scale parameters retrievable from SHG measurements may be relevant markers to indicate the progression neurodegenerative disorders, including glaucoma. So far for the purpose of both research and clinical diagnosis, only systemic loss of microtubules could be detected and no method exists to monitor the nanoscopic alterations in the microtubule patterns.

The method and systems described herein permit one to determine the microtubule patterns in the retinal tissue on the nanoscopic scales by measuring the differential response of microtubules to multiple conditions of excitation light.

In one embodiment, the polarization of the excitation light is set with an optical element (e.g. 304 of FIG. 3), such as wave-plate and/or polarizer, before the scanning beam, and the returned second-harmonic light is recorded for each polarization. In one embodiment, there is a second optical element (e.g. 614, 622) before the detector, such as wave-plate and/or polarizer, which selects a certain polarization of the returned light. The difference in the detected signal is analyzed to obtain individual tensor elements of the second-order susceptibility $\chi^{(2)}$.

In another embodiment, a spatial mode of the excitation light is set with an optical element (e.g. 304), such as spatial light modulator and/or phase plate, before the scanning beam, and the returned second-harmonic light is recorded for each spatial mode. The amplitude (or intensity) distribution of a laser beam in space is referred to as spatial mode. Given the symmetry of optical system, a certain group of spatial modes exist. The most widely known example is Hermite-Gaussian modes, which are a family of 2D transverse modes also known as $TEM_{pq}$, where p and q are integer indices associated with each spatial coordinates. For the purpose of investigating light-matter interactions, another more complex family of spatial modes is often employed, i.e. Laguerre-Gaussian mode, which has an azimuthal angular dependence of $e^{-il\phi}$ where I is the azimuthal mode index. The Laguerre-Guassian mode possesses a well-defined orbital angular momentum, and is thus capable of imparting torque to material medium in a similar way as the polarization of light can. Conversely, the spatial mode of light beam is altered during the interaction with matter, which provides a means to measure the material property. In one embodiment, there is a second optical element (e.g. 314, 622) before the detector, which selects a certain spatial mode of the returned light. The difference in the detected signal is analyzed to obtain individual tensor elements of the second-order susceptibility $\chi^{(2)}$.

In yet another embodiment, the center wavelength of the light is set with an optical element (e.g. 304), such as filter, prisms, and/or gratings, before the scanning beam, and the returned second-harmonic light is recorded for each wavelength. In one embodiment, there is a second optical element (e.g. 314, 622) before the detector, such as filter, prisms, and/or gratings, which selects a certain wavelength of the returned light. The difference in the detected signal is analyzed to obtain individual tensor elements of the second-order susceptibility $\chi^{(2)}$.

Figure 7:
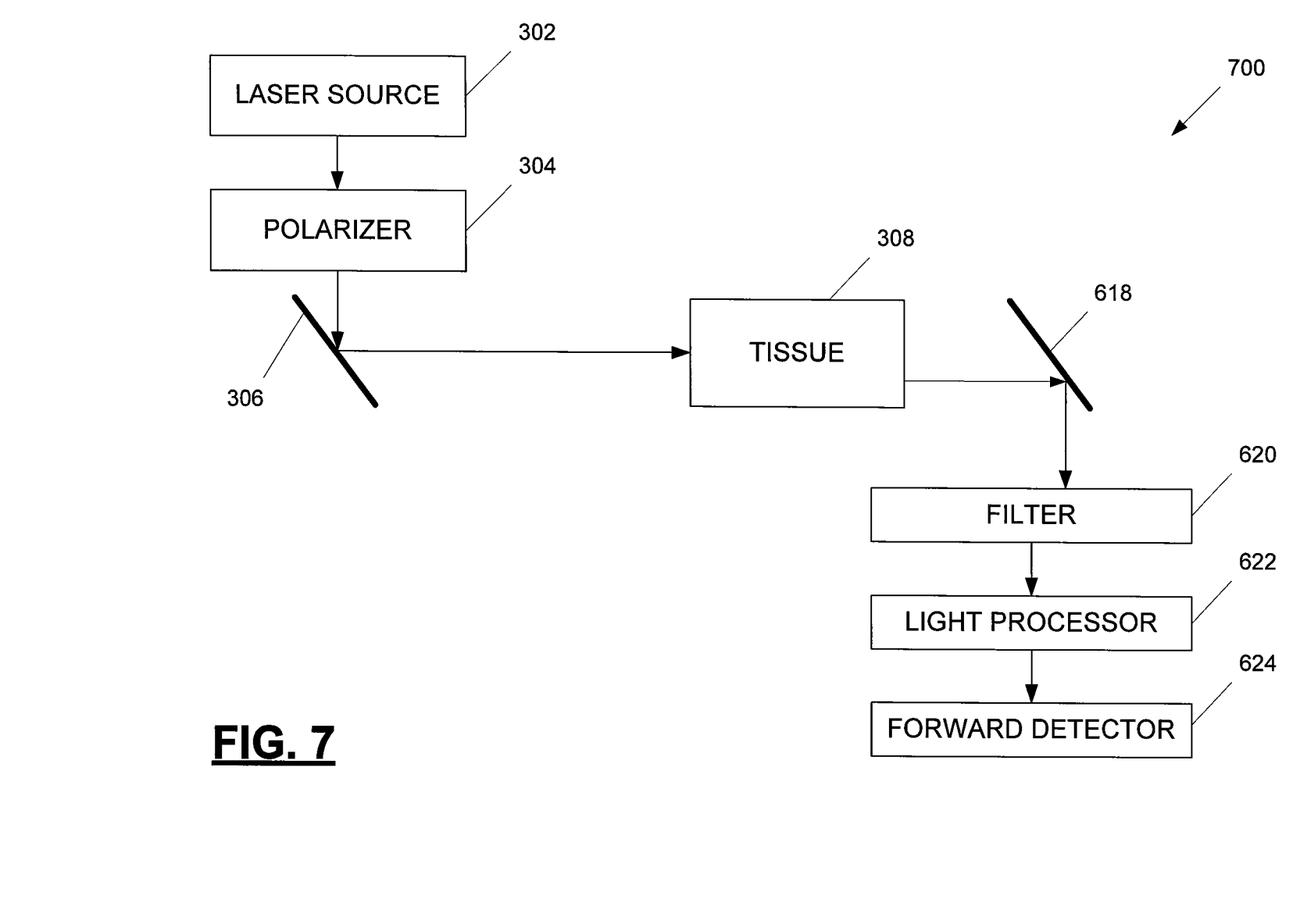
FIG. 7 is another schematic depiction of an exemplary system for determining a microtubule pattern in a retinal tissue.

FIG. 7 is a schematic depiction of an exemplary system 700 for determining a microtubule pattern in a retinal tissue using label-free second-harmonic generation microscopy. System 700 is analogous to system 600 of FIG. 6 but does not examine the backward-propagating light and only examines the forward-propagating light. The emitted radiation from second-harmonic generation is predominantly forward-propagating. For SHG imaging of the retina through the pupil, this property imposes a significant technical challenge. It is possible for the emitted radiated produced in the microtubules to be returned in the backward direction, i.e. the opposite direction to the excitation light, by backscattering in the medium located in the forward direction after the microtubules. In an intact eye, the backscattering of the SHG emission can occur in the underlying layers such as the choroid and sclera. However, due to the anatomical variations among populations and even within a single fundus, analyzing the backscattered light cannot be readily standardized, which is particularly problematic for screening new drugs. At least some of the systems disclosed herein allow the effect of drugs on the microtubule patterns in the retinal tissue to be precisely determined by measuring the forward-propagating light through the microtubules.

Figure 8A:
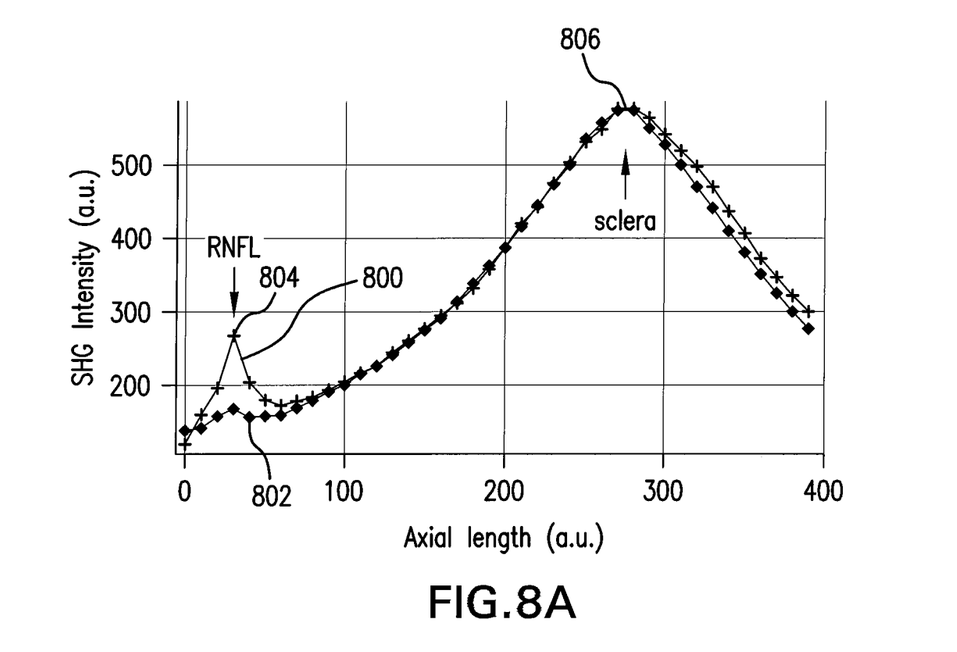
Figure 8B:
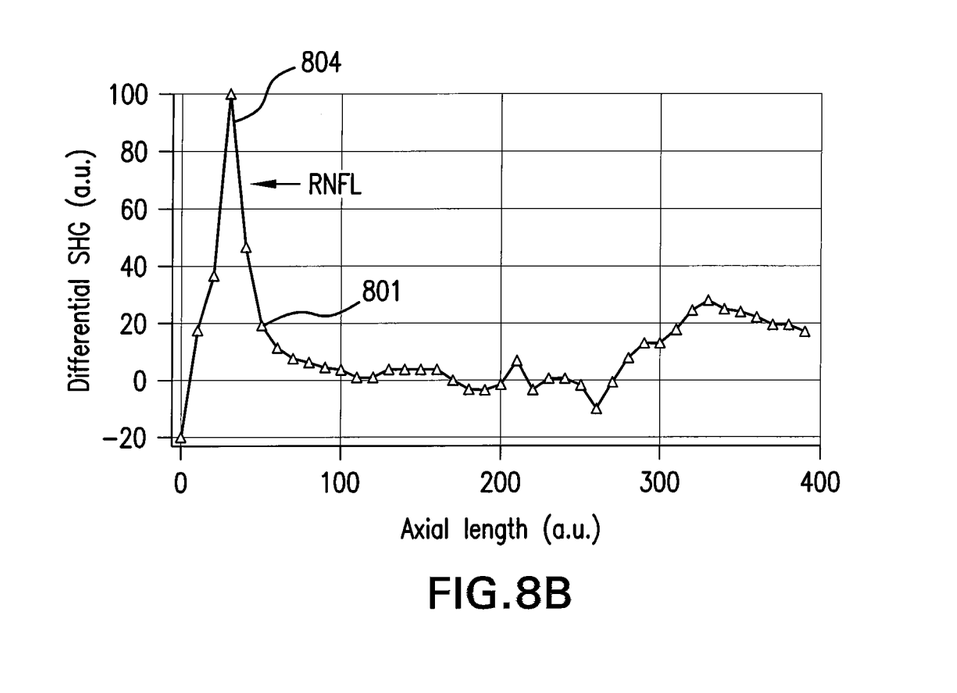
FIG. 8B is a graph showing the difference between the two different polarization states of FIG. 8A.

Referring to FIG. 8A and FIG. 8B, the intensity second-harmonic generating signal from retinal ganglion cells signal depends on the polarization of excitation wavelength. It is possible to utilize the optical properties of second-harmonic generation microscopy from the retinal nerve fibers to enhance the contrast of second-harmonic generation images. For instance, FIG. 8A depicts improvement of the second-harmonic generation contrast for the retinal nerve fiber layer by polarization-dependence of second-harmonic generation microscopy. Thickness scans 802, 804 are acquired for two linear polarization states of the excitation beam, e.g. 0 and 90 degrees. The scans traversed a retinal nerve fiber layer region 800 and a sclera region 806. The first polarization state 802 and the second polarization state 804 had substantially the same second-harmonic generation signal intensity over sclera region 806. In contrast, the first polarization state 802 and the second polarization state 804 had different intensity responses over retinal nerve fiber layer region 804 due to the orientation of the microtubules with respect to the polarized light. By selecting appropriate set of excitation polarizations and taking the difference a microtubule pattern within the retinal nerve fiber layer was determined. FIG. 8B is a graph of the difference signal 801 showing the difference in intensities between the first and second polarization states 802, 804 of FIG. 8A. The microtubule tubule pattern that was determined shows the presence of a large concentration of uniformly orientated microtubules at retinal nerve fiber layer region 804 and the lack of such microtubules elsewhere along difference signal 801. This illustrates that an algorithm for signal processing can be devised to enhance the second-harmonic generation contrast specifically for the retinal nerve fiber layer.

The morphology of retinal nerve fiber layer is generally unaffected by depolymerization of microtubules. Accordingly, the techniques described in this specification permit the detection of microtubule depolymerization at a molecular level before morphological changes in the retinal nerve fiber layer are evident in the macroscopic tissue. Analysis of the alterations in the characteristics (e.g. polarization, spatial mode) of the generated light are even more sensitive and can provide advance warning of microtubule changes, even before the overall microtubule pattern is detectably changed.

The spatial pattern of microtubule degradation in the retinal nerve fiber layer was studied to determine whether decrease in second-harmonic generation signal from the retinal nerve fiber layer is caused by shrinking of the tissue volume. The cross section of retinal nerve fibers was examined following treatment with nocodazole. The retinal nerve fiber layer morphology did not appear to change while the intensity of microtubule second-harmonic generation signal is significantly reduced during the same period. This result suggests that the shape of the retinal nerve fiber layer remains intact even while the architecture of microtubule assembly is compromised.

EXAMPLE 1

Microtubular Second-Harmonic Generation Imaging in Zebrafish Retina

The integrity of microtubular structure in a live cell is maintained by active regulation of polymerization and depolymerization rates. Adult zebrafish (2 yrs old) were used because of the extended viability under anesthesia. The animals were anesthetized with MS-222, the lens was removed, and the posterior pole was imaged using the methods described in this specification. The microtubule second-harmonic generation signal from the nerves in retinal nerve fiber layer was determined and visualized. Although the focus level was adjusted axially, it is possible that second-harmonic generation image also included an unknown amount of contribution from the adjacent collagenous layer, because of the moderate depth of focus and the small radius of curvature of the zebrafish eye.

EXAMPLE 2

Microtubular Second-Harmonic Generation Imaging in Rat Retina

Rat retinal flat-mounts were prepared from euthanized rats. The eyes were enucleated. A circumferential incision was made around the limbus and the cornea, lens, and vitreous humor were removed. Several radial cuts were made in the eye cup. The retina was isolated from the retinal pigment epithelium and the sclera and transferred to buffered Ames' medium (Sigma-Aldrich), which was bubbled with 95% oxygen and 5% carbon dioxide, and maintained at 34° C. and pH 7.4. The sample was transferred to a perfusion chamber with a transparent bottom (Warner Instruments) within 15 minutes after euthanasia. The retina was placed on the microscope stage with the retinal nerve fiber layer side up. The speed of laminar flow was approximate 1 mL per min. To examine the gross morphology after second-harmonic generation imaging, the retina was fixed with 4% paraformaldehyde (PFA) in phosphate buffered saline (PBS) and 10% sucrose.

Imaging: Simultaneous second-harmonic generation microscopy and two-photon excitation fluorescence microscopy were performed to image the fresh retina. The excitation wavelength utilized short pulses from a mode-locked Ti:Sapphire laser source with a duration of 100 fs at 80-MHz repetition rate. The excitation wavelength was 785 nm, except for the experiments where two excitation wavelengths at 785 and 880 nm are compared. A Pockel cell was employed to attenuate the laser beam and also to rapidly switch it off during galvanometer's return travel. The polarization of the excitation beam was controlled with a half- or quarter-wave plate. The laser beam was focused with a water immersion objective lens (Olympus XLUMP1anFL 20×/1.0 NA) on an upright microscope (Sutter Instrument). The average power P was 55-120 mW at the sample. The corresponding average intensity was 60-130 $MW/cm^2$, where w is the 1/e-radius of the Gaussian profile of two-photon excitation. The full width at half-maximum of the excitation focus was 0.28 and 1.11 microns in the transverse and axial dimension, respectively. The pixel dwell time was approximately 4.4 microseconds.

Fluorescence was detected in the backward beam path, which included a set of spectral filters (Chroma Technology), and photomultiplier tube (PMT) detectors (Hamamatsu). Second-harmonic generation light was acquired both in the forward and backward directions. Second-harmonic generation images were generally obtained in the forward detection. The forward detection path consists of a high-NA objective lens (Olympus UApo340 40×/1.35 NA), dichroic and band-pass filters, and a PMT detector. The second-harmonic generation channels had a filter with a narrow bandwidth (22 nm) centered at half the excitation wavelength, whereas the fluorescence channel had a broad transmission in the 450-550 nm range. All detection paths employed a non-descanned mode. Once detection paths are aligned, the sample was translated with an automated stage (ASI). Images were averaged over 3-5 scans.

Pharmacology: The relationship between the structure of the microtubule assembly and microtubule second-harmonic generation intensity was studied by using nocodazole, a pharmacological agent that hinders polymerization of the microtubules. After a baseline period during which the samples were perfused with medium alone, perfusion was performed with medium containing 25-11M nocodazole (Sigma-Aldrich) and 0.4% dimethylsulfoxide (DMSO, Sigma-Aldrich). Control samples were continuously perfused in medium containing only 0.4% DMSO. The durations of baseline and treatment period were 40 and 90 minutes, respectively.

Time-lapse second-harmonic generation imaging of the retinal nerves was performed every 5 min. Optical sections were acquired over the same region of interest (ROI) that are 1.5 or 2 microns apart in a depth range of 60-80 microns, so that the entire thickness of the nerve fiber bundle was imaged. After data acquisition, image registration was performed to correct for the drift motion of sample and second-harmonic generation intensity was integrated over a volume of pixels.

Image processing: Post-processing and image analysis was done using ImageJ and Matlab. Mosaic of images was constructed using a version of ImageJ with stitching plugins (Fiji). For volumetric reconstruction, the orthogonal views were created from optical sections (N=50) acquired with 3 micrometer axial spacing. The thickness of retinal nerve fiber layer was evaluated using the following automatic procedure which eliminates observer's bias. First, a stack of grayscale second-harmonic generation images was converted to binary images by thresholding. The threshold level was then determined using an iterative intermeans algorithm. Finally the pixel value was summed over the z dimension and then multiplied by the spacing between slices to obtain the retinal nerve fiber layer thickness.

Results: A microtubule pattern within the retina was successfully obtained using the second-harmonic generation microscopy methods described in this specification.

While the invention has been described with reference to certain embodiments, it will be understood by those skilled in the art that various changes may be made and equivalents may be substituted for elements thereof to adapt to particular situations without departing from the scope of the disclosure. Therefore, it is intended that the claims not be limited to the particular embodiments disclosed, but that the claims will include all embodiments falling within the scope and spirit of the appended claims.

What is claimed is:

1. A method for screening drugs in a retinal tissue using label-free second-harmonic generation microscopy, the retinal tissue having a retinal nerve fiber layer comprising microtubules, the method comprising:
    exposing the retinal tissue to a drug;
    emitting a pulsed laser light having an excitation wavelength and a predetermined first polarization or a predetermined first spatial mode;
    scanning the retinal tissue with the pulsed laser light, at least some of the microtubules producing generated light with a second-harmonic wavelength that is half the excitation wavelength;
    measuring a generated polarization or a generated spatial mode of the generated light;
    determining a difference between (a) the first polarization and the generated polarization or (b) the first spatial mode and the generated spatial mode; and
    determining whether or not the drug impacts the retinal tissue based on the difference.

2. The method as recited in claim 1, further comprising filtering out extraneous wavelengths to select only the second-harmonic wavelength.

3. The method as recited in claim 1, wherein the generated light comprises forward-propagating light and backward-propagating light, the scanning the retinal tissue further comprises detecting only the forward-propagating light.

4. The method as recited in claim 1, wherein the retinal nerve fiber layer has a thickness and the scanning the retinal tissue further comprises the pulsed laser light through the thickness.

5. The method as recited in claim 1, further comprising determining a second-order susceptibility ($\chi^{(2)}$) based on the difference.

6. The method as recited in claim 1, wherein the scanning the retinal tissue scans at the excitation wavelength within a bandwidth of about 10 nm.

7. The method as recited in claim 1, further comprising determining an orientation axis of the at least some of the microtubules.

8. The method as recited in claim 1, further comprising determining a first microtubule pattern within the retinal tissue based on the second-harmonic wavelength.

9. The method as recited in claim 1, further comprising determining a chiral angle of the at least some of the microtubules.

10. The method as recited in claim 8, further comprising:
    scanning the retinal tissue with a second pulsed laser light at the excitation wavelength, the second pulsed laser light having a second polarization different from the first polarization, at least some of the microtubules producing generated light; and
    determining a second microtubule pattern within the retinal tissue based on the generated second-harmonic wavelength from the second polarization.

11. The method as recited in claim 8, further comprising comparing the first microtubule pattern to a predetermined standard.

12. The method as recited in claim 11, wherein the predetermined standard is a second microtubule pattern that was obtained prior to the determining the first microtubule pattern.

13. The method as recited in claim 9, further comprising determining a first microtubule pattern within the retinal tissue based on the second-harmonic wavelength.

14. The method as recited in claim 13, further comprising
    determining a second microtubule pattern after a predetermined period of time has passed; and
    comparing the first microtubule pattern to the second microtubule pattern.

15. The method as recited in claim 13, further comprising visualizing the first microtubule pattern by providing an image of the first microtubule pattern.

16. A method for screening drugs in a retinal tissue using label-free second-harmonic generation microscopy, the retinal tissue having a retinal nerve fiber layer comprising microtubules, the method comprising:
    exposing the retinal tissue to a drug;
    emitting a pulsed laser light having an excitation wavelength and a predetermined first spatial mode;
    scanning the retinal tissue with the pulsed laser light, at least some of the microtubules producing generated light with a second-harmonic wavelength that is half the excitation wavelength;
    measuring a generated spatial mode of the generated light;
    determining a difference between the first spatial mode and the generated spatial mode; and
    determining whether or not the drug impacts the retinal tissue based on the difference.

17. The method as recited in claim 16, wherein the spatial mode is a Laguerre-Gaussian mode.

18. A method for determining a microtubule pattern in a retinal tissue using label-free second-harmonic generation microscopy, the retinal tissue having a retinal nerve fiber layer comprising microtubules, the method comprising:
    emitting a pulsed laser light having an excitation wavelength and a predetermined first polarization or a predetermined first spatial mode;
    scanning the retinal tissue with the pulsed laser light, at least some of the microtubules producing generated light with a second-harmonic wavelength that is half the excitation wavelength;
    measuring a generated polarization or a generated spatial mode of the generated light;
    determining a difference between (a) the first polarization and the generated polarization or (b) the first spatial mode and the generated spatial mode; and
    determining a microtubule pattern within the retinal tissue based on the second-harmonic wavelength.

* * * * *

UNITED STATES PATENT AND TRADEMARK OFFICE
CERTIFICATE OF CORRECTION

| | | |
|---|---|---|
| PATENT NO. | : 9,134,300 B2 | Page 1 of 1 |
| APPLICATION NO. | : 14/306898 | |
| DATED | : September 15, 2015 | |
| INVENTOR(S) | : Danias et al. | |

It is certified that error appears in the above-identified patent and that said Letters Patent is hereby corrected as shown below:

In the Claims:

Column 12, line 66, that portion of claim 4 reading "-comprising the pulsed laser light-" should read "--comprising scanning the pulsed laser light--"

Signed and Sealed this
Nineteenth Day of January, 2016

Michelle K. Lee
*Director of the United States Patent and Trademark Office*